(12) United States Patent
Tronnes (10) Patent No.: US 8,478,424 B2
(45) Date of Patent: Jul. 2, 2013

(54) MEDICAL LEAD HAVING COAXIAL CONNECTOR

(75) Inventor: Carole Tronnes, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 574 days.

(21) Appl. No.: 12/707,311

(22) Filed: Feb. 17, 2010

(65) Prior Publication Data

US 2010/0217365 A1 Aug. 26, 2010

Related U.S. Application Data (60) Provisional application No. 61/154,458, filed on Feb. 23, 2009.

(51) Int. Cl.
*A61N 1/372* (2006.01)

(52) U.S. Cl.
USPC .......................................................... 607/116

(58) Field of Classification Search
USPC .......................................................... 607/116
See application file for complete search history.

(56) References Cited

U.S. PATENT DOCUMENTS

| | | | |
|---|---|---|---|
| 5,241,957 A * | 9/1993 | Camps et al. | 607/119 |
| 5,265,623 A * | 11/1993 | Kroll et al. | 607/122 |
| 5,354,326 A | 10/1994 | Comben et al. | |
| 6,157,862 A | 12/2000 | Brownlee et al. | |
| 6,216,045 B1 | 4/2001 | Black et al. | |
| 6,374,476 B1 | 4/2002 | Ponzi et al. | |
| 6,489,562 B1 | 12/2002 | Hess et al. | |
| 7,184,838 B2 | 2/2007 | Cross, Jr. | |
| 7,302,299 B2 | 11/2007 | Wojciechowicz | |
| 2001/0016702 A1 | 8/2001 | Benjamin | |
| 2006/0271136 A1 | 11/2006 | Wojciechowicz | |
| 2007/0225784 A1 | 9/2007 | Bly et al. | |
| 2008/0097193 A1 * | 4/2008 | Karmarkar | 600/423 |

* cited by examiner

*Primary Examiner* — Eric D. Bertram (57) ABSTRACT

A medical lead includes a connector for operably coupling the lead to an active medical device. The connector includes a first tubular conductive contact having a length, a proximal end, a distal end and a lumen extending through the contact from the proximal end to the distal end. The connector also includes a second tubular conductive contact having a length, a proximal end, and a distal end. The length of the second contact is greater than the length of the first contact. The second contact is disposed in the lumen of the first contact such that the proximal and distal ends of the second contact extend beyond the proximal and distal ends of the first contact. The lead further includes first and second electrodes. The first electrode is operably coupled to the first contact, and the second electrode is operably coupled to the second contact.

28 Claims, 9 Drawing Sheets

MEDICAL LEAD HAVING COAXIAL CONNECTOR

RELATED APPLICATION

This application claims the benefit of priority to U.S. Provisional Application No. 61/154,458, filed on Feb. 23, 2009, which application is hereby incorporated herein by reference in its entirety to the extent that it does not conflict with the disclosure presented herein.

FIELD

This application relates to medical devices, more particularly medical leads.

BACKGROUND

Electrical stimulation technology is expanding in scope, resulting in therapies that implant leads in more and more areas of the body. However, before undergoing complex surgery associated with permanently implanting an electrical signal generator and medical lead, a patient or their health care provider may want to determine whether the patient may be responsive to therapy associated with such implantable medical systems.

Temporary or trial leads may be employed to determine whether a patient is a candidate for electrical stimulation therapy. The temporary lead can be implanted in the patient such that a distal end containing an electrode is positioned in proximity to a tissue to which the therapeutic electrical signal is to be delivered. The proximal end of the lead remains external to the patient and can be connected to an external signal generator so that electrical signals may be delivered to the target tissue via the lead.

One therapy where trial leads are currently employed is sacral nerve stimulation. Currently unipolar leads with a single electrode are used for trialing purposes to determine whether the patient would be a good candidate for therapy with an implantable electrical signal generator. A ground pad is adhered to the skin of the patient to complete the circuit and allow the temporary trial therapy to be tested. If the ground pad falls off the patient's skin, the circuit cannot be completed and the therapy cannot be effectively tested. Bipolar trialing leads and systems would be desirable. However, as additional wires are added to the leads to couple electrodes to contacts designed to electrically couple the lead to the trial stimulator, the thickness and complexity of the lead increases.

The thickness of the trialing lead can be determinative as to whether the temporary lead is implanted in a physician's office or in the operating room. For purposes of convenience and cost, it is often desirable to implant a lead in a doctor's office as opposed to an operating room. While there are no clear guidelines regarding where an implant procedure is to be performed, physicians are often uncomfortable implanting a temporary lead if an introducer having a gauge smaller than (or thicker than) a 20-gauge needle. The inner diameter of typical 20-gauge needles is about 0.035 inches (about 0.9 millimeters). Thus, it is desirable to keep trialing leads to a diameter of less than about 0.03 inches (about 0.75 millimeters). Adding additional contacts, electrodes, and wires to make a bipolar trialing lead, while maintaining a small profile, presents a difficult challenge.

BRIEF SUMMARY

Among other things, bipolar leads capable of having small outer diameters are described herein. The leads may be useful as trialing leads and include low profile co-axial contacts to maintain a small overall outer dimension of the leads. Methods for manufacturing such leads are also described herein.

In various embodiments, a medical lead, as described herein, includes a proximal connector for operably coupling the lead to an active medical device. The connector includes a first tubular conductive contact having a length, a proximal end, a distal end and a lumen extending through the contact from the proximal end to the distal end. The connector also includes a second tubular conductive contact having a length, a proximal end, and a distal end. The length of the second contact is greater than the length of the first contact. The second contact is disposed in the lumen of the first contact such that the proximal end of the second contact extends beyond the proximal end of the first contact. The distal end of the second contact may align with, extend beyond or terminate proximal to the distal end of the first contact. The lead further includes first and second electrodes. The first electrode is operably coupled to the first contact, and the second electrode is operably coupled to the second contact. The first and second electrodes may be formed from un-insulated portions of first and second and insulated conductive wires. The conductive wires may be electrically coupled to the contacts. The lead may further include a first insulating tube having a proximal end and a distal end. The first insulating tube is disposed about the second contact such that the distal end of the insulating tube extends beyond the distal end of the second contact and the proximal end of the insulating tube is disposed about the second contact between the proximal and distal ends of the second contact, leaving the proximal end of the second contact un-insulated. The proximal end of the first insulating tube may extend beyond the proximal end of the first contact. The lead may further include a second insulating tube having a proximal end and a distal end. The second insulating tube is disposed about the first contact such that the distal end of the insulating tube extends beyond the distal end of the first contact and the proximal end of the insulating tube is disposed about the first contact between the proximal and distal ends of the first contact, leaving the proximal end of the first contact un-insulated.

In various embodiments, a method for manufacturing a lead, as described herein, includes attaching a first conductive wire to a first tubular contact. The first contact has a proximal end, a distal end and a lumen extending through the contact from the proximal end to the distal end. The method further includes attaching a second conductive wire to a second tubular contact. The second contact has a proximal end and a distal end. The method further includes disposing a first insulating shrink tubing about the second tubular contact such that the distal end of the shrink tubing extends beyond the distal end of the second contact and the proximal end of the shrink tubing is disposed about the second contact between the proximal and distal ends. The first insulating tubing is shrunk around the second contact to produce a partially insulated second contact having an un-insulated proximal portion and an insulated distal portion. The partially insulated second contact is inserted into the lumen of the first contact such that the un-insulated proximal portion extends beyond the proximal end of the first contact. The method further includes disposing a second insulating shrink tubing about the first tubular contact such that the distal end of the shrink tubing extends beyond the distal end of the first contact and the proximal end of the shrink tubing is disposed about the first contact between the proximal and distal ends. The second insulating tubing is shrunk around the first contact to produce a partially insulated first contact having an un-insulated proximal portion and an insulated distal portion.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used herein "substantially" means to a great extent or degree. Thus, two items or characteristics that are substantially the same are the same to a great extent or degree. For example, the two items or characteristics may be the same to the extent that processes for producing the things or characteristics are reproducible. Alternatively, or in addition, two things or characteristics that are substantially the same may be generally indistinguishable when considered for their intended purpose or purposes. For example, if two sections of a lead are to have substantially the same outer diameter so that the lead may be slidably disposed in an introducer with tight tolerances, then if the both sections slide through the introducer without difficulty the two outer diameters can be considered substantially the same.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to medical leads having co-axial contacts. The leads may be fully implantable or partially implantable for trialing purposes. An electrode is electrically coupled to each of the co-axial contacts.

Leads as described herein may be used in conjunction with any suitable electrical medical device, such as an electrical signal generator system or a monitoring system. Examples of electrical signal generator systems that such leads may be used with include spinal cord stimulators, gastric stimulators, sacral nerve stimulators, deep brain stimulators, cochlear implants, defibrillators, pacemakers, and the like. In many embodiments, such electrical medical devices are implantable. In various embodiments, such electrical devices are external devices and used for purposes of determining whether a patient may be a good candidate for an implantable system.

Figure 1A:
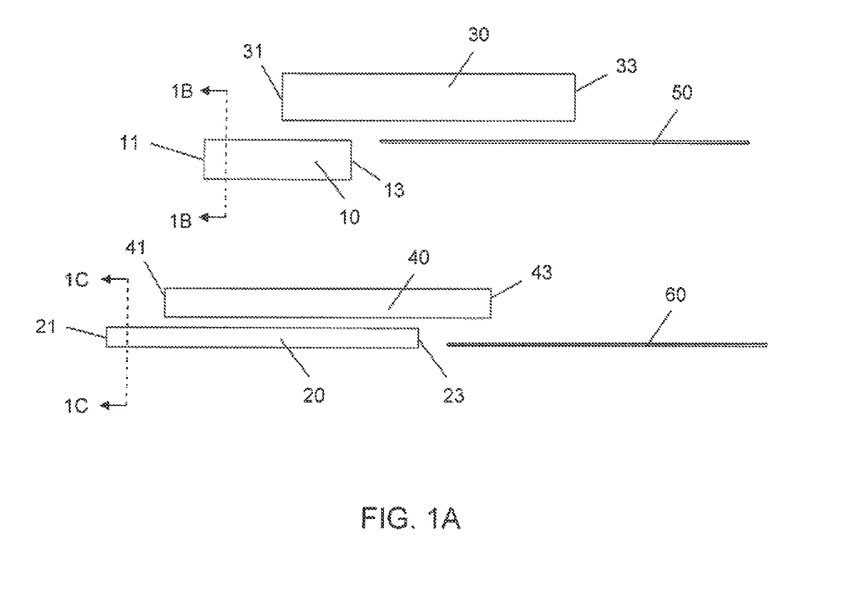
FIG. 1A is a schematic illustration of an exploded side view of representative components for forming a lead having a coaxial connector.
Figure 1B:
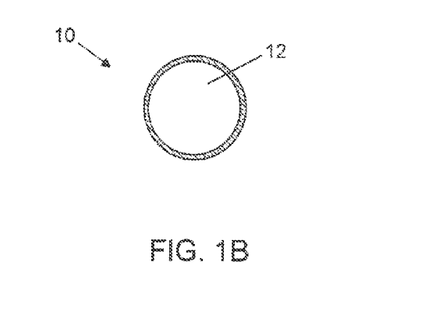
FIGS. 1B-C are schematic illustrations of cross sections taken through tubular contacts at lines 1B-1B and 1C-1C, respectively, of FIG. 1A.
Figure 1C:
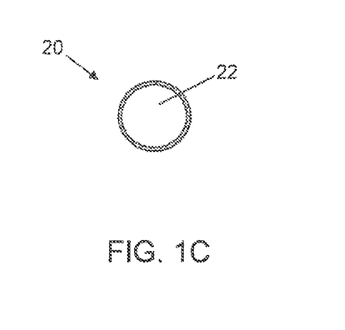

Referring now to FIG. 1A, illustrated is an exploded side view of selected representative components that may be used to make a lead having a coaxial connector. Such components include first 10 and second 20 tubular conductive contacts, first 40 and second 30 electrically insulating tubes and first 50 and second 60 conductive wires. The conductive tubular contacts 10, 20 may be formed of any suitable conductive material such as stainless steel, platinum, platinum iridium, titanium, tantalum, nickel-cobalt-molybdenum alloys, or the like and may be formed in any suitable manner, such as drawing. The first and second tubular contacts 10, 20 each have proximal 11, 21 and distal 13, 23 ends and form lumens 13, 23 (see FIGS. 1B-C) that extend from the proximal end 11, 21 to distal 13, 23 end. The conductive wires 50, 60 may similarly be formed of any suitable conductive material such as stainless steel, platinum, platinum iridium, titanium, tantalum, nickel-cobalt-molybdenum alloys, or the like. In various embodiments, the conductive wires 50, 60 are braided stranded wires. Preferably, the wires 50, 60 are insulated with any suitable material, such as ethylene tetrafluoroethylene (ETFE). The wires 50, 60 are electrically coupled to the conductors 10, in any suitable manner, such as welding, soldering, crimping, or the like. The first insulating tube 40 is configured to be placed about the second tubular contact 20 and serves to electrically insulate the second contact 20 form the first contact 10. In the final form of the lead, the first insulating tube 40 is disposed about the second contact 20 and is disposed within a lumen of the first contact 10, e.g., as described in more detail below. The second insulating tube 30 is configured to be disposed about the first tubular contact 10. The insulating tubes 50, 60 may be made of any suitable insulating material, such as polyester, fluoropolymer, silicone, urethane, polyolefin, or the like. In some embodiments, one or both of the insulating tubes 50, 60 are shrink tubing, such as polyester shrink tubing.

Figure 2A:
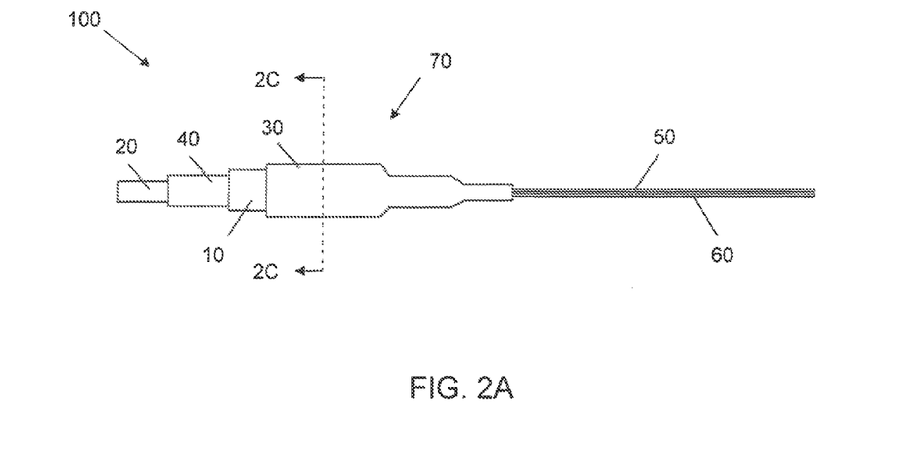
FIG. 2A is a schematic illustration of a side view of a lead having a coaxial connector region.
Figure 2B:
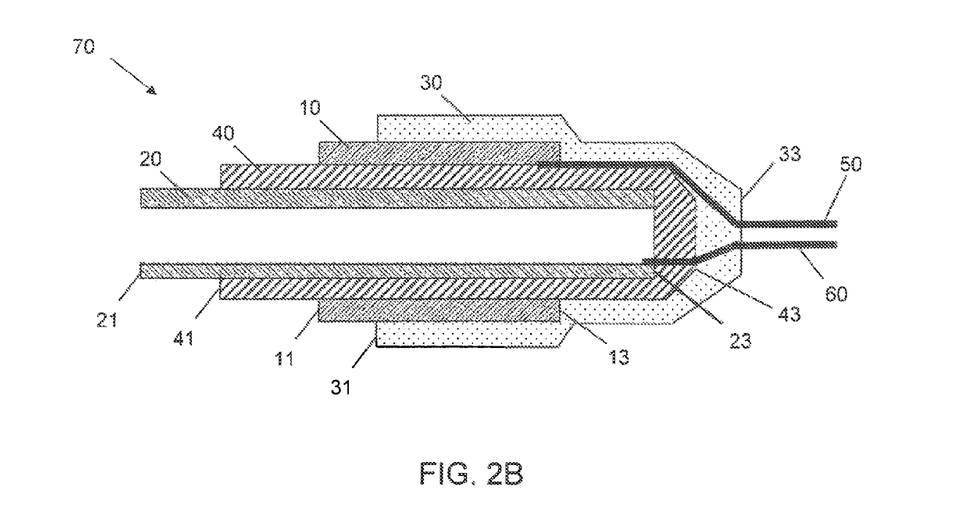
FIG. 2B is a schematic illustration of a longitudinal section of the lead of FIG. 2A.
Figure 2C:
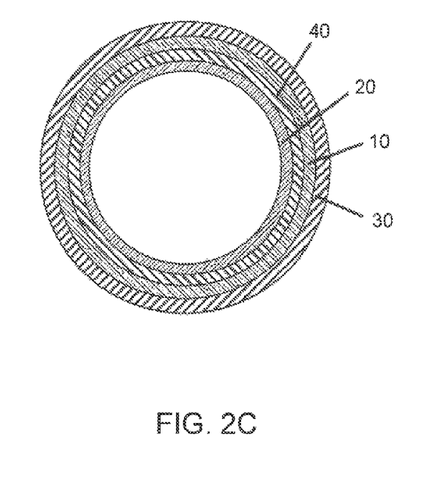
FIG. 2C is a schematic illustration of a cross-section taken through line 2C-2C of FIG. 2A.

Referring now to FIG. 2, schematics of a side view (A), a longitudinal sectional view (B), and a radial sectional view (C) of a representative lead 100, or portion thereof, are shown.

The lead 100 includes a proximal connector portion 70 for electrically coupling the lead to an electrical medical device, such as an electrical signal generator. The second tubular contact 20 is disposed in the lumen of, and coaxial with, the first contact 10. The second contact 20 is longer than the first contact 10, and the proximal end 21 of the second contact 20 extends beyond the proximal end 11 of the first contact 10. In the depicted embodiment the distal end 22 of the second tubular contact 20 extends beyond the distal end 12 of the first tubular contact 10. Such a configuration may be desirable when insulating tubes 30, 40 do not provide a great deal of structural support; e.g., when insulating tubes 30, 40 are formed from shrink tubing, such that the distal portion of the first contact 20 provides an area for gripping so that connector region 70 may be sufficiently pushed into a receptacle of an electrical medical device to couple distal portions of contact 10, 20 to the electrical device.

The first insulating tube 40 is disposed between the first 10 and second 20 contacts to electrically isolate the coaxially disposed contacts. The proximal end 41 of the first insulating tube 40 is disposed about the second contact 20 between the proximal 21 and distal 22 ends of the contact 20, leaving a proximal end portion of the second contact 20 un-insulated so that the contact 20 may be electrically coupled with an internal contact of an electrical medical device, such as an electrical signal generator. In the depicted embodiment, the distal end 43 of the first insulating tube 40 extends beyond the distal end 23 of the second contact 20, and the first insulating tubing 40 is made of shrink tubing that has been shrunk. Similarly, the second insulating tube 30 is made of shrink tubing that has been shrunk in the embodiment depicted in FIG. 2. The second insulating tube 30 is disposed about the first tubular contact 10. The proximal end 31 of the second insulating tube 30 is disposed about the first contact 10 between the proximal end 11 and the distal end 13 of the contact 10, leaving a proximal portion of the first contact 10 un-insulated and capable of electrically coupling with a contact of an electrical medical device. In the depicted embodiment, the distal end 33 of the second insulating tubing 30 extends beyond the distal end 13 of the first contact 10, beyond the distal end 23 of the second contact 20, and beyond the distal end 43 of the first insulating tube 40, to provide an outer surface to the connector region 70.

In the embodiment depicted in FIGS. 2A-C, tight tolerances exist between the second contact 20 and the first insulator 40, the first insulator 40 and the first contact 10, and the first contact 10 and the second insulator 30. While not shown, it will be understood that a suitable adhesive may be used to bond the first insulating tubing 40 to the first or second contact or may be used to bond the second insulating tubing 30 to the first contact. When the first 40 and second 30 insulating tubes are made from shrunk shrink tubing, the insulating tubes 40, 30 snuggly engage the second 20, and first 10 contacts and have been found to sufficiently prevent lateral movement between the first 10 and second 20 contacts.

Figure 3:
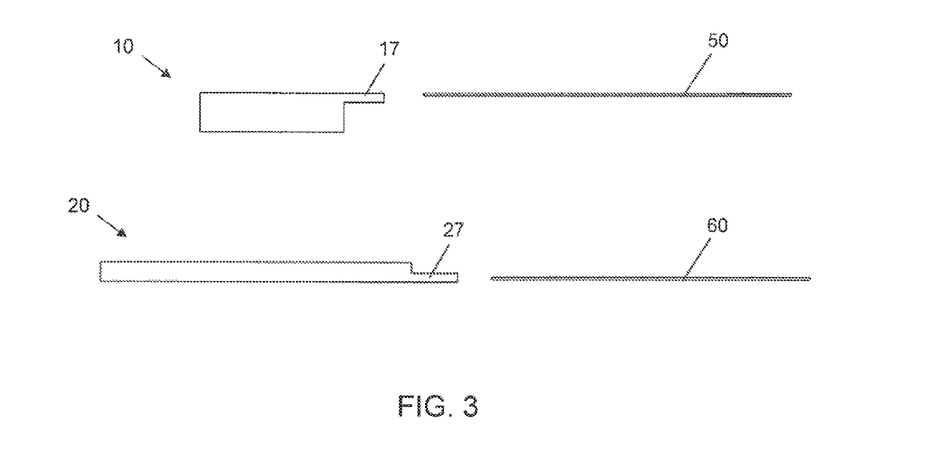
FIG. 3 is a schematic illustration of side views showing tubular contacts with extensions.

With reference to FIG. 3, the first contact 10 may include a distal extension tab 17 to facilitate coupling the first conductive wire 50 to the first contact 10. Similarly, the second contact 20 may include a distal extension tab 27 to facilitate coupling the second conductive wire 60 to the second contact 20. The extension tabs 17, 27 may be formed with the initial formation of the tubular contacts 10, 20 or may be formed after the formation of the tubular contacts 10, 20 by cutting, etching, welding, or the like.

Figure 4:
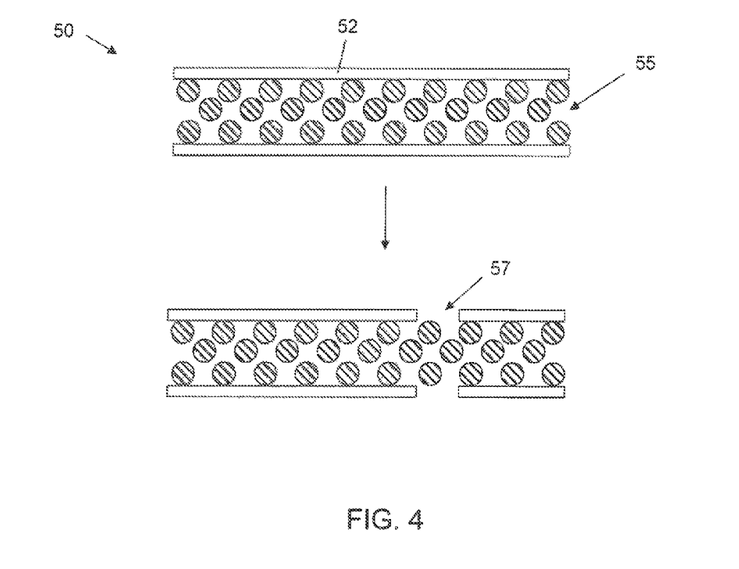
FIG. 4 is a schematic illustration of a cross-sectional view of an insulated braided strand wire having a portion of the insulating material removed to expose the conductive wire and form an electrode.

With reference to FIG. 4, an electrode 57 may be formed in an insulative conductive wire 50 by removing a portion of the outer insulating material 52 to expose the wire 55, in the depicted case, a braided stranded wire 55.

Figure 5:
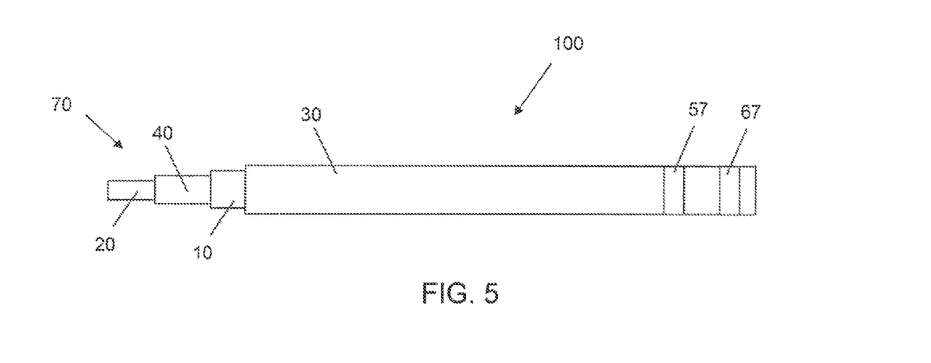
FIG. 5 is a schematic illustration of a side view of a representative lead having a coaxial connector region.

With reference to FIG. 5, a lead 100 having a coaxial conductor portion 70 as described herein may include ring electrodes 57, 67. It will be understood that any suitable electrode type or form may be employed. The first ring electrode 57 is electrically coupled to the first contact 10 via a conductive wire. The second ring electrode 67 is electrically coupled to the second contact 20 via a conductive wire. In the depicted embodiment, the second insulating tube 40 extends to the distal end of the lead 100.

It will be understood that the use of numerical identifiers, such as first and second contacts and first and second electrodes, can be arbitrary as used herein, are used for convenience, and do not necessarily indicate an ordering from proximal to distal, unless specifically stated. By way of example and with reference to FIG. 5, the first contact 10 may be electrically coupled to or with the first 57 (most proximal) electrode or the second 67 (most distal) electrode. Similarly, the second contact 20 may be electrically coupled to or with the first 57 (most proximal) electrode or the second 67 (most distal) electrode. Thus, the "first" electrode may be the proximal 57 or the distal 67 electrode depicted in, e.g., FIG. 5, and the "second" electrode may be the proximal 57 or distal 67 electrode depicted in, e.g., FIG. 5.

Figure 6:
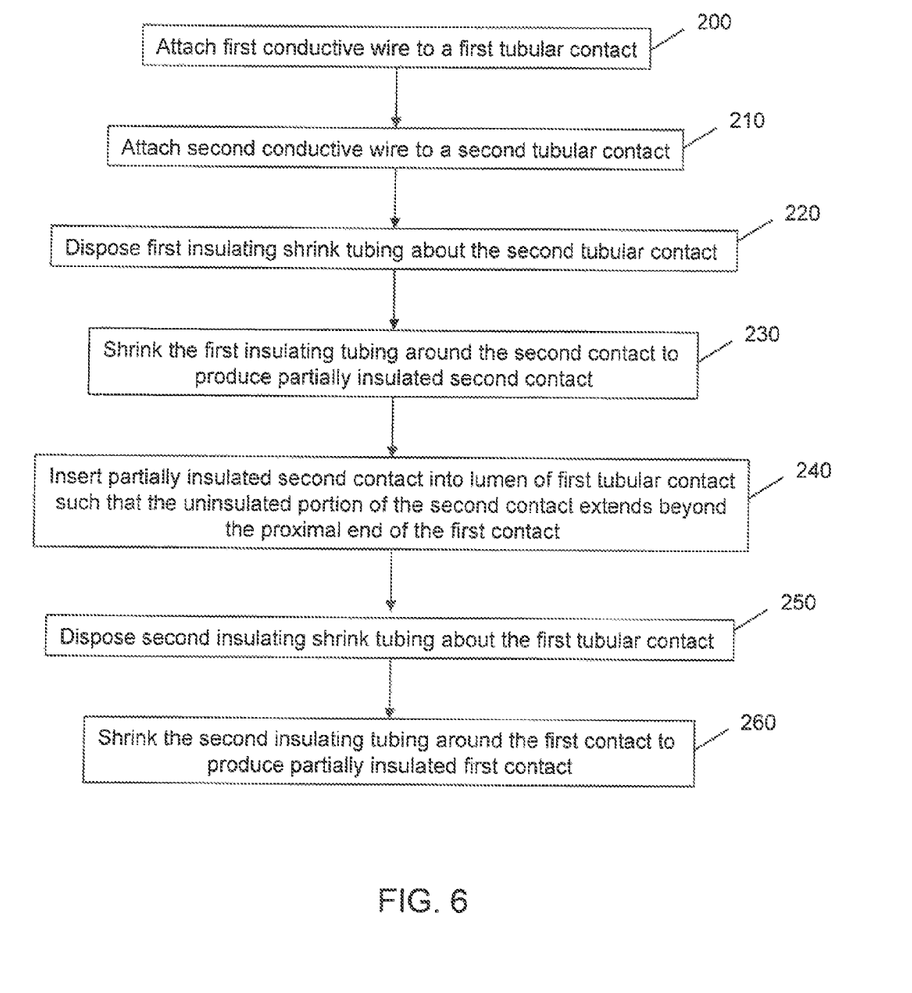
FIG. 6 is a flow diagram of a representative method for manufacturing a lead.

Leads having co-axial connectors as described above may be made via any suitable process. For purposes of illustration and with reference to FIG. 6, one representative method is described in more detail below. In the method depicted in FIG. 6, a first conductive wire; e.g., an insulated braided strand wire, is attached or electrically coupled to a first tubular conductor (200); e.g., via welding, soldering, crimping, or the like. The first tubular contact has a proximal end, a distal end and a lumen extending through the contact from the proximal end to the distal end; e.g., as described above. The depicted method further includes attaching a second conductive wire to a second tubular contact (210). The second contact has a proximal end and a distal end. A first insulating shrink tubing is disposed about the second tubular contact (220). In various embodiments, the first insulating shrink tubing is disposed about the second tubular contact such that the distal end of the shrink tubing extends beyond the distal end of the second contact and the proximal end of the shrink tubing is disposed about the second contact between the proximal and distal ends. The depicted method further includes shrinking the first insulating tubing around the second contact to produce a partially insulated second contact having an uninsulated proximal portion and an insulated distal portion (230). The partially insulated second contact is inserted into the lumen of the first contact such that the uninsulated proximal portion extends beyond the proximal end of the first contact (240). A second insulating shrink tubing is disposed about the first tubular contact (250). In various embodiments, the second insulating shrink tubing is disposed about the first tubular contact such that the distal end of the shrink tubing extends beyond the distal end of the first contact and the proximal end of the shrink tubing is disposed about the first contact between the proximal and distal ends. The depicted method further includes shrinking the second insulating tubing around the first contact to produce a partially insulated first contact having an uninsulated proximal portion and an insulated distal portion (260).

The first conductive wire generally extends distally from the first contact, and the second insulating shrink tube may, in various embodiments, be disposed about at least a portion of the first wire distal the first contact and may be shrunk around the first wire. The second conductive wire generally extends distally from the second contact, and the first insulating shrink tube may, in various embodiments, be disposed about at least a portion of the second wire distal the second contact and may be shrunk around the first wire. In various embodiments, the first and second wires are insulated and electrodes are formed by removing a portion of the insulation to expose the conductive wire and form the electrode.

Leads having co-axial conductors as described above may be used for any suitable purpose. For purposes of illustration, use of such leads in trial stimulation of a sacral nerve to determine whether a patient may be a candidate for sacral nerve stimulation via an implantable system is described.

Figure 7:
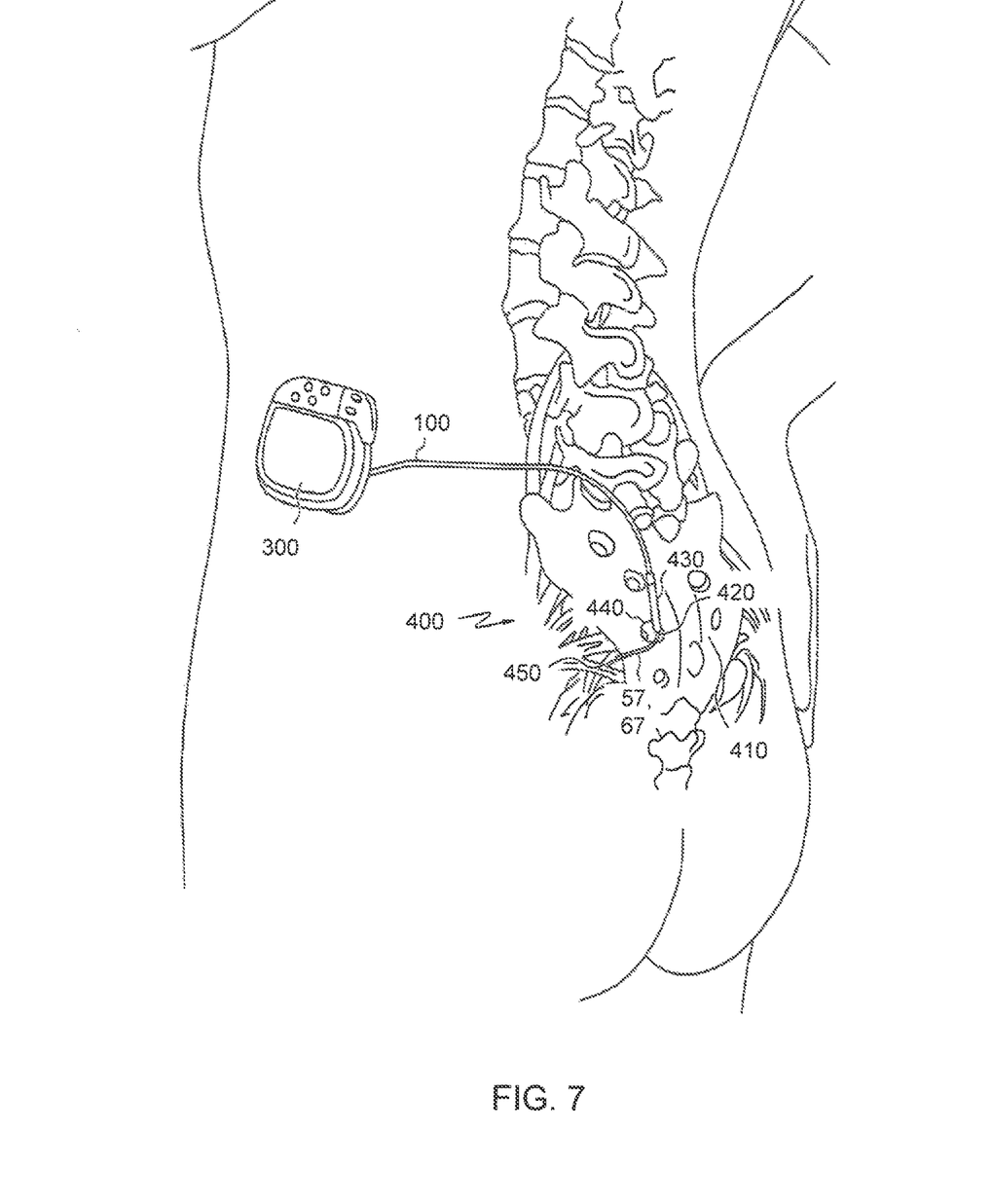
FIG. 7 is a schematic illustration of a trial lead partially implanted in a patient and coupled to an external electrical signal generator.

FIG. 7 shows an embodiment of an external electrical signal generator 300 configured to apply a therapeutic electrical signal to sacral nerves 400 located near the sacrum 410. The sacral nerves are accessible through an entry point 420 along an insertion path 430 into a foramen 440 to reach a desired location 450. The electrical signal generator system includes a lead 100. The lead 100 has electrodes 56, 67 positioned at or near, generally in proximity to, the distal end to apply electrical signals to the nerves and a coaxial connector (not shown) at the proximal end to connect to the trial neurostimulator 300. The lead 100 may have any suitable outer dimension. Preferably, the lead 100 does not exceed an outer diameter of about 0.03 inches (0.75 millimeters) along its length. In some embodiments, the lead 100 does not exceed an outer diameter of about 0.025 inches (0.64 millimeters) along its length. While not shown, it will be understood that a lead extension or cable may be used to connect the lead 100 to the signal generator 300.

Figure 8A:
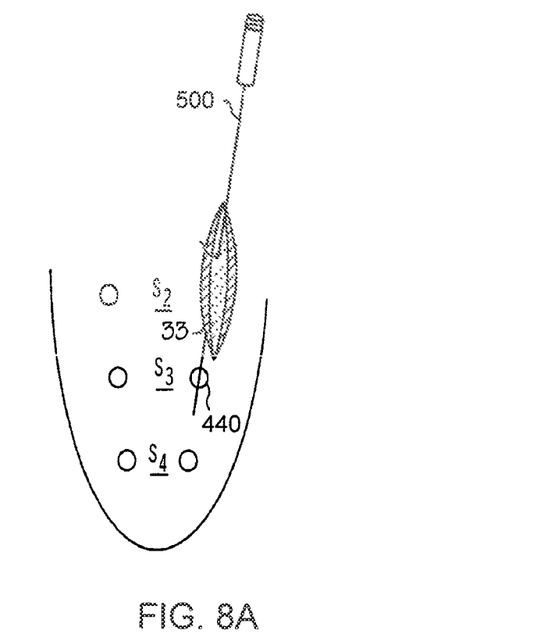
FIG. 8A is a schematic illustration showing a needle being inserted into a foramen.
Figure 8B:
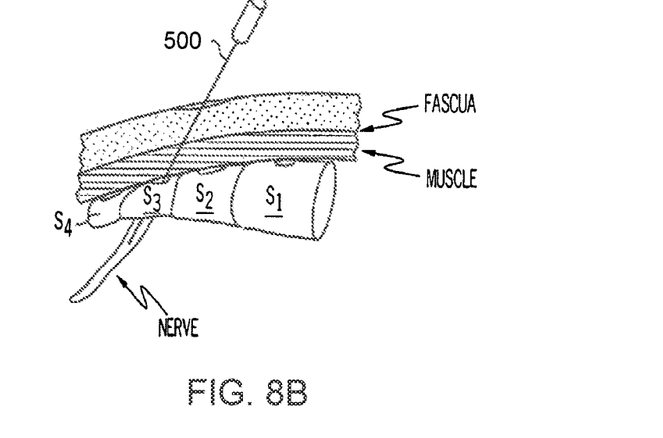
FIG. 8B is a schematic illustration of a cross section of the view of FIG. 8A.

Referring now to FIGS. 8A-E, a representative method for implanting a lead 100 for sacral nerve stimulation is shown. Additional details regarding some suitable methods of implanting a lead for sacral nerve stimulation are provided in, e.g., U.S. Patent Application Pre-Grant Publication No. 2005/0240238, entitled "Minimally invasive apparatus for implanting sacral nerve stimulation lead", Oct. 27, 2005, and U.S. Patent Application Pre-Grant Publication No. 2007/0255370, entitled "Implantable medical electrical stimulation lead, such as PNE lead, and method of use", Nov. 1, 2007, which applications are hereby incorporated herein by reference in their respective entireties to the extent that they do not conflict with the disclosure presented herein. As shown in FIGS. 8A-B, a small incision may be made in the patient's lower back in proximity to the sacral vertebrae. A needle 500 is inserted through the incision and through foramen 440 adjacent a sacral nerve. The needle 500 is selected based upon the needs of the patient and typically ranges in size from an outer diameter of about 26 gauge (0.46 mm) to about 12 gauge (2.80 mm) such as the 20 gauge (0.89 mm), thin wall, foramen needle Models 041828 and 041829 available from Medtronic, Inc. (Minneapolis, Minn.). The foramen needle may include a stylet, also known as an obturator, in the needle central opening and can include markings that measure, e.g., 1.0 cm increments and a wider mark at 5.0 cm, to aid in positioning needle depth. Additionally the needle 500 tip and proximal portion adjacent to the hub may be conductive, so a trial stimulator can be electrically connected to the hub. The trial stimulator stimulation signal will travel to the foramen needle tip to evoke a response from the patient to determine if the foramen needle 500 is properly positioned.

Figure 8C:
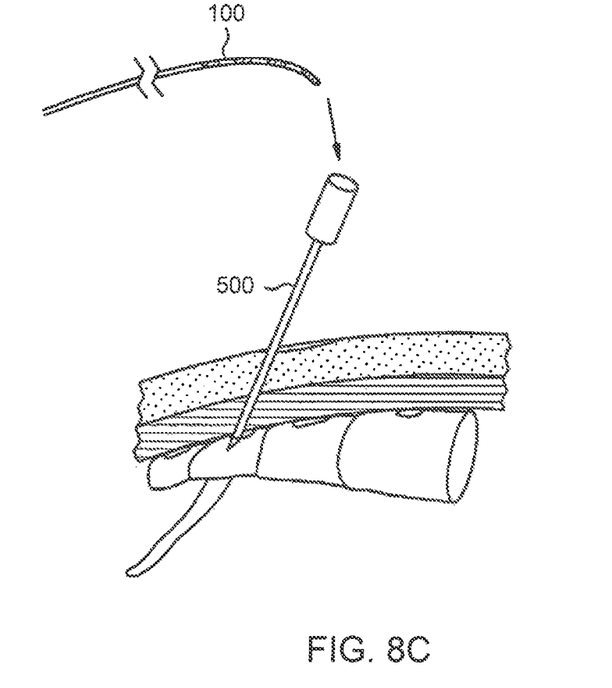
FIGS. 8C-D are schematic illustrations showing a lead being inserted into the needle shown in FIG. 8B.
Figure 8D:
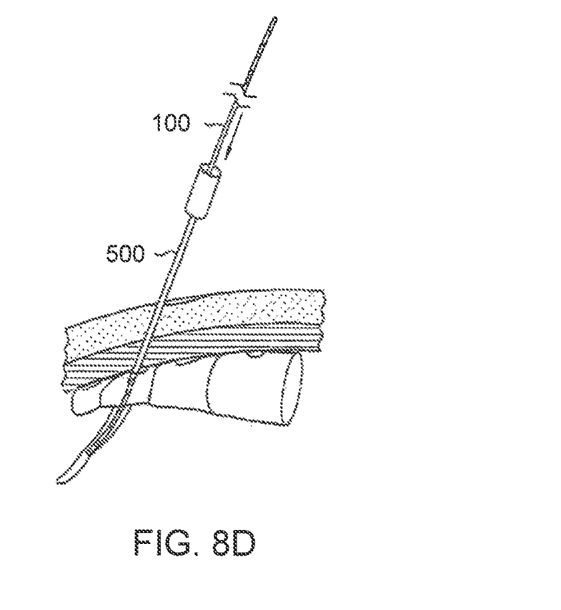
Figure 8E:
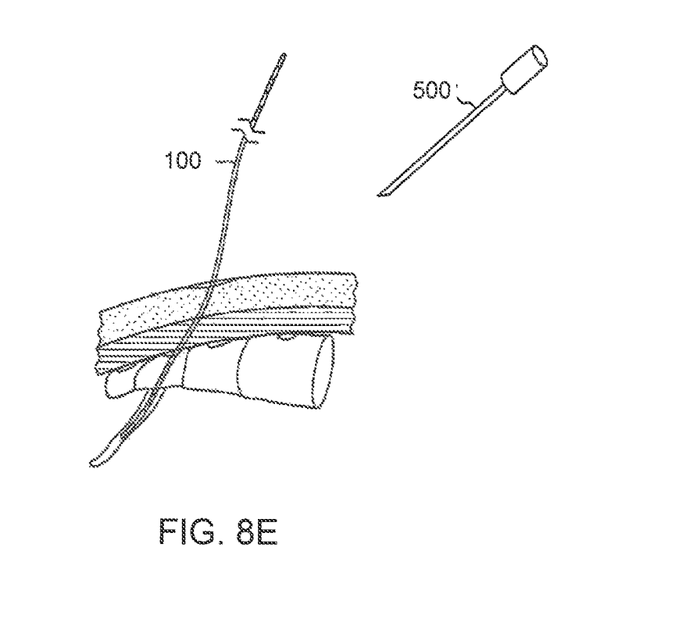
FIG. 8E is a schematic illustration showing a needle being withdrawn over the lead depicted in FIG. 8D.

When the needle 500 is properly positioned, the obturator (not shown) may be removed and the trial lead 100 may be inserted into the needle (FIGS. 8C-D). The lead 100 may be connected to the trial stimulator to determine if the lead is properly positioned. Once the lead is properly positioned, the needle 500 may be withdrawn over the lead 100 (FIG. 8E).

The lead 100 may then be reconnected to the external electrical signal generator and trial stimulation may proceed.

Thus, embodiments of the MEDICAL LEAD HAVING COAXIAL CONNECTOR are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:
1. A medical lead comprising:
a connector for operably coupling the lead to an active medical device, the connector including
a first tubular conductive contact having a length, a proximal end, a distal end and a lumen extending through the contact from the proximal end to the distal end,
a second tubular conductive contact having a length, a proximal end, and a distal end, and
a first insulating tube having a proximal end and a distal end, and disposed about the second contact such that the distal end of the insulating tube extends beyond the distal end of the second contact and the proximal end of the insulating tube is disposed about the second contact between the proximal and distal ends of the second contact, leaving the proximal end of the second contact un-insulated,
wherein the second contact is disposed in the lumen of the first contact such that the proximal and distal ends of the second contact extend beyond the proximal and distal ends of the first contact;
a first electrode operably coupled to the first contact; and
a second electrode operably coupled to the second contact.
2. The medical lead according to claim 1, wherein the proximal end of the first insulating tube extends beyond the proximal end of the first contact.
3. A medical lead according to claim 1, wherein the first electrode is formed from an uninsulated portion of an insulated conductive wire, wherein the wire is electrically coupled to the first contact.
4. A medical lead according to claim 1, wherein the second electrode is formed from an uninsulated portion of an insulated conductive wire, wherein the wire is electrically coupled to the second contact.
5. A medical lead according to claim 1, wherein the lead has an outer diameter along its length of about 0.025 inches or less.
6. A medical lead according to claim 1, wherein the lead is configured to be temporarily and partially implanted in a patient and is configured to apply an electrical signal from an external electrical signal generator to a sacral nerve of the patient.
7. A medical lead according to claim 1, further comprising a first conductive wire electrically coupling the first contact to the first electrode, and a second conductive wire electrically coupling the second contact to the second electrode.
8. A medical lead according to claim 1, wherein the connector is configured to be received by a receptacle of an electrical signal generator such that the first and second contacts are electrically coupled to the signal generator, wherein the distal end of the second contact extends beyond the receptacle when the first and second contacts are electrically coupled to the signal generator.
9. A medical lead according to claim 1, wherein the length of the second contact is greater than the length of the first contact.

10. A method comprising:
introducing a distal end of a lead according to claim 1 into a 20-gauge introducer needle; and
withdrawing the introducer needle over a proximal end of the lead.

11. A medical lead comprising:
a connector for operably coupling the lead to an active medical device, the connector including
a first tubular conductive contact having a length, a proximal end, a distal end and a lumen extending through the contact from the proximal end to the distal end,
a second tubular conductive contact having a length, a proximal end, and a distal end, and
a first insulating tube having a proximal end and a distal end disposed between the first and second electrical contacts to electrically insulate the first and second contacts, and
a second insulating tube having a proximal end and a distal end, wherein the second insulating tube is disposed about the first contact such that the distal end of the insulating tube extends beyond the distal end of the first contact and the proximal end of the insulating tube is disposed about the first contact between the proximal and distal ends of the first contact, leaving the proximal end of the first contact un-insulated,
wherein the second contact is disposed in the lumen of the first contact such that the proximal and distal ends of the second contact extend beyond the proximal and distal ends of the first contact;
a first electrode operably coupled to the first contact; and
a second electrode operably coupled to the second contact.

12. A medical lead according to claim 11, wherein the first electrode is formed from an uninsulated portion of an insulated conductive wire, wherein the wire is electrically coupled to the first contact.

13. A medical lead according to claim 11, wherein the second electrode is formed from an uninsulated portion of an insulated conductive wire, wherein the wire is electrically coupled to the second contact.

14. A medical lead according to claim 11, wherein the lead has an outer diameter along its length of about 0.025 inches or less.

15. A medical lead according to claim 11, wherein the lead is configured to be temporarily and partially implanted in a patient and is configured to apply an electrical signal from an external electrical signal generator to a sacral nerve of the patient.

16. A medical lead according to claim 11, further comprising a first conductive wire electrically coupling the first contact to the first electrode, and a second conductive wire electrically coupling the second contact to the second electrode.

17. A medical lead according to claim 11, wherein the connector is configured to be received by a receptacle of an electrical signal generator such that the first and second contacts are electrically coupled to the signal generator, wherein the distal end of the second contact extends beyond the receptacle when the first and second contacts are electrically coupled to the signal generator.

18. A medical lead according to claim 11, wherein the length of the second contact is greater than the length of the first contact.

19. A method comprising:
introducing a distal end of a lead according to claim 11 into a 20-gauge introducer needle; and
withdrawing the introducer needle over a proximal end of the lead.

20. A medical lead comprising:
a connector for operably coupling the lead to an active medical device, the connector including
a first tubular conductive contact having a length, a proximal end, a distal end and a lumen extending through the contact from the proximal end to the distal end,
a second tubular conductive contact having a length, a proximal end, and a distal end, and
wherein the second contact is disposed in the lumen of the first contact such that the proximal and distal ends of the second contact extend beyond the proximal and distal ends of the first contact;
a first electrode operably coupled to the first contact; and
a second electrode operably coupled to the second contact,
wherein the connector is configured to be received by a receptacle of an electrical signal generator such that the first and second contacts are electrically coupled to the signal generator, wherein the distal end of the second contact extends beyond the receptacle when the first and second contacts are electrically coupled to the signal generator.

21. A medical lead according to claim 20, wherein the first electrode is formed from an uninsulated portion of an insulated conductive wire, wherein the wire is electrically coupled to the first contact.

22. A medical lead according to claim 20, wherein the second electrode is formed from an uninsulated portion of an insulated conductive wire, wherein the wire is electrically coupled to the second contact.

23. A medical lead according to claim 20, further comprising a first insulating tube disposed between the first and second electrical contacts to electrically insulate the first and second contacts.

24. A medical lead according to claim 20, wherein the lead has an outer diameter along its length of about 0.025 inches or less.

25. A medical lead according to claim 20, wherein the lead is configured to be temporarily and partially implanted in a patient and is configured to apply an electrical signal from an external electrical signal generator to a sacral nerve of the patient.

26. A medical lead according to claim 20, further comprising a first conductive wire electrically coupling the first contact to the first electrode, and a second conductive wire electrically coupling the second contact to the second electrode.

27. A medical lead according to claim 20, wherein the length of the second contact is greater than the length of the first contact.

28. A method comprising:
introducing a distal end of a lead according to claim 20 into a 20-gauge introducer needle; and
withdrawing the introducer needle over a proximal end of the lead.

* * * * *